(12) United States Patent
McElwain

(10) Patent No.: US 6,261,603 B1
(45) Date of Patent: Jul. 17, 2001

(54) SKIN CREAM

(76) Inventor: Elizena A. McElwain, 125 Picnic La., Hardinsburg, KY (US) 40143

( * ) Notice: Subject to any disclaimer, the term of this patent is extended or adjusted under 35 U.S.C. 154(b) by 0 days.

(21) Appl. No.: 09/546,544

(22) Filed: Apr. 10, 2000

Related U.S. Application Data

(60) Provisional application No. 60/133,813, filed on May 11, 1999.

(51) Int. Cl.7 .................................................. A61K 35/178
(52) U.S. Cl. ............................ 424/522; 424/59; 424/401; 424/725; 514/725; 514/773; 514/776; 514/777; 514/780; 514/784; 514/844; 514/846; 514/847; 514/873
(58) Field of Search .................................. 424/59, 195.1, 424/401, 522; 514/725, 773, 776, 777, 783, 784, 844, 846, 847, 873, 780

(56) References Cited

U.S. PATENT DOCUMENTS

| | | | |
|---|---|---|---|
| 4,999,195 | * | 3/1991 | Hayes .................................. 424/114 |
| 5,153,230 | | 10/1992 | Jaffery . |
| 5,254,331 | | 10/1993 | Mausner . |
| 5,322,685 | | 6/1994 | Nakagawa et al. . |
| 5,360,824 | | 11/1994 | Barker . |
| 5,372,815 | * | 12/1994 | Hodutu ................................ 424/401 |
| 5,391,373 | | 2/1995 | Mausner . |
| 5,470,874 | * | 11/1995 | Lerner .................................. 514/474 |
| 5,571,503 | | 11/1996 | Mausner . |
| 5,578,312 | * | 11/1996 | Parrinello ............................ 424/401 |
| 5,658,580 | | 8/1997 | Mausner . |
| 5,939,457 | * | 8/1999 | Miser .................................. 514/557 |
| 6,113,891 | * | 9/2000 | Burdick et el. .................... 424/70.13 |

FOREIGN PATENT DOCUMENTS

| | | |
|---|---|---|
| 56-139409 | 10/1981 | (JP) . |
| 59-139267 | 8/1984 | (JP) . |
| 61-76413 | 4/1986 | (JP) . |
| 839542 | 6/1981 | (RU) . |

* cited by examiner

Primary Examiner—Francisco Prats
Assistant Examiner—Kailash C. Srivastava
(74) Attorney, Agent, or Firm—Richard C. Litman

(57) ABSTRACT

Topical skin rejuvenation cream and lotion compositions for dry, damaged or aging skin comprising deionized water, mink oil, vitamin E, retinol acetate (vitamin A), ginseng, aloe vera, glycerin, lanolin (hydrous), gotu kola, soybean oil, fish liver oil, hydrolyzed animal protein, dl-alpha tocopherol acetate, stearic acid, cetyl alcohol, citric acid, silicon, isopropylmyristate, propylene glycol, stearyl alcohol, glycerol stearate, dimethicone, lactic acid, quaternium-15, propylparaben, carbomer 934 and 940, triethanolamine, methylparaben, tetrasodium ethylenediaminetetraacetic acid (EDTA), DMDM hydantoin, diazolidinyl urea and fragrance.

7 Claims, No Drawings

SKIN CREAM

CROSS-REFERENCE TO RELATED APPLICATION

This application claims the benefit of U.S. Provisional Patent Application Ser. No. 60/133,813, filed May 11, 1999.

BACKGROUND OF THE INVENTION

1. Field of the Invention

The present invention relates to a skin rejuvenation cream and lotion especially beneficial for dry, damaged or aging skin.

2. Description of Related Art

The need for anti-aging creams/lotions and moisturizers without a prescription is strongly felt. RETIN-A is used to reduce wrinkles but has a high incidence of side effects and requires a prescription. Over-the-counter skin care preparations generally do not suffice, and often make the skin feel greasy. Their moisturizing qualities also tend to vanish quickly, resulting in dry, cracked skin.

U.S. Pat. No. 5,153,230 issued to Jaffery on Oct. 6, 1992 discloses a topical skin cream composition. The skin cream of Jaffery is designed to prevent and treat aging skin. The active ingredient is glycolic acid in concentrations up to 3.5 weight percent. The composition also may include vitamin A palmitate and/or vitamin E acetate. Preservatives are included in the composition to increase shelf life. Other ingredients may be included in the composition but no natural ingredients such as mink oil, soybean oil, fish liver oil, or gotu kola are included in the composition.

U.S. Pat. No. 5,254,331 issued to Mausner on Oct. 19, 1993 describes a skin cream composition designed to minimize environmental stress on the skin, improve firmness and elasticity, and counteract dryness. The appearance of wrinkles and other cosmetically undesirable effects on the skin is prevented or delayed, as well as correcting existing wrinkles. The skin cream of Mausner contains a protein complex with serum proteins and hydrolyzed animal proteins; a protein-amino acid-vitamin-nucleotide complex with propylene glycol, serum proteins, niacinamide, water, adenosine phosphate, and arginine; and a dimethylsilanoyl hyaluronate complex.

U.S. Pat. No. 5,391,373 issued to Mausner on Feb. 21, 1995 discloses a skin cream composition which provides retexturization, produces smoothness, minimizes age spots, improves color, and increases firmness and moisture content of the skin. The composition comprises sodium lactate; a micellar complex comprising horse chestnut extract, Crataegus extract, water, panthenol, propylene glycol, phospholipids, phenoxyethanol, glycosphingolipids, chlorphenesin, and cholesterol; a protein complex comprising serum proteins, hydrolyzed animal proteins, and glycogen; a carbohydrate-based complex comprising dextran, glycine, and glucosamine; a long-chain fatty acid ester of retinol; a long-chain fatty acid ester of ascorbic acid; and a short-chain fatty acid ester of tocopherol. Other cosmetic components may be included.

U.S. Pat. No. 5,571,503 issued to Mausner on Nov. 5, 1996 describes an anti-pollution cosmetic composition which provides significant protection against moisture loss and damage due to free radical activity and ultraviolet light. The composition contains an anti-pollution complex with propylene glycol, hydrolyzed wheat protein, mannitol, glycogen, yeast extract, ginseng extract, linden extract, calcium pantothenate, horse chestnut extract, and biotin; a micellar complex with phospholipids, glycosphingolipids, panthenol, Crataegus extract, cholesterol, and sodium hyaluronate; an anti-free radical complex with melanin, a short-chain fatty acid ester of tocopherol, a long-chain fatty acid ester of retinol, and a long-chain fatty acid ester of ascorbic acid; and a sun screen. Other cosmetic components may be included.

U.S. Pat. No. 5,658,580 issued to Mausner on Aug. 19, 1997 describes a skin cream composition which provides significant retexturization of the skin, smooths the skin, minimizes age spots, improves skin color, increases skin firmness and moisturizes the skin. The skin cream composition contains sodium lactate; a long-chain fatty acid ester of ascorbic acid; a short-chain carboxylic acid ester of tocopherol; witch hazel; and horsetail extract.

The patents referenced herein do not disclose the same topical cream and lotion compositions as those of the present invention. The skin rejuvenation cream and lotion of the present invention is better able to soften and rejuvenate the skin. The skin rejuvenation cream and lotion compositions of the present invention are specifically designed to moisturize and hide wrinkled or broken skin.

None of the above inventions and patents, taken either singly or in combination, is seen to describe the instant invention as claimed.

SUMMARY OF THE INVENTION

The skin rejuvenation cream and lotion compositions of the current invention include a unique composition with rich emollients that help to prevent wrinkles by locking in moisture, and by firming and toning the skin. The present invention is to be applied daily on the skin to obtain soft, smooth and silky skin. The compositions includes deionized water, mink oil, vitamin E, retinol acetate (vitamin A), borage oil, ginseng, aloe vera, lanolin (hydrous), gotu kola, soybean oil, fish liver oil, hydrolyzed animal protein, dl-alpha tocopherol acetate, stearic acid, cetyl alcohol, citric acid, silicon, isopropylmyristate, propylene glycol, stearyl alcohol, glycerol stearate, dimethicone, lactic acid, quaternium-15, propylparaben, carbomer 934 and 940, triethanolamine, methylparaben, tetrasodium ethylenediaminetetraacetic acid (EDTA), DMDM hydantoin, diazolidinyl urea and fragrance.

Accordingly, it is a principal object of the invention to provide topical cream and lotion compositions for applying to the skin to smooth fine lines and wrinkles.

It is another object of the invention to develop a pleasant feeling skin moisturizer.

It is a further object of the invention to provide topical skin cream and lotion compositions that reduce the signs of aging.

Still another object of the invention is to provide a topical skin cream and lotion composition that leaves the skin feeling soft and silky to the touch.

It is an object of the invention to provide improved components and arrangements thereof in a topical composition for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention pertains to a safe and effective topical skin rejuvenation cream and lotion compositions which are designed to reduce dryness and aid in repair of aging skin. The skin cream and lotion compositions are also beneficial for normal skin to prevent dryness and the effects of aging. The compositions of the current invention have both moisturizing and anti-aging effects.

The skin rejuvenation cream and lotion compositions of the invention contain a cream base of preferably (unless otherwise indicated) about 8 parts of a cream base component. The cream base component is preferably the cream available under the trade name Personal Care Cream. Personal Care Cream has the following ingredients: deionized water, stearic acid, cetyl alcohol, isopropyl alcohol, isopropyl myristate, propylene glycol, retinol acetate, stearyl alcohol, glycerol stearate, dimethicone, hydrolyzed animal protein, lactic acid, carbomer 934, triethanolamine, methylparaben, quaternium-15, propylparaben, and fragrance. The skin rejuvenation cream and lotion composition further includes preferably about 0.5 part to about 1 part mink oil (preferably Weather Spirits brand), preferably about 0.05 part to about 0.1 part ginseng (preferably Spring Valley), about 1 part Aloe Vera Gel (preferably Fruit of the Earth brand), about 1 part lanolin hydrous (preferably all natural), preferably about 0.03 part to about 0.06 part gotu kola (preferably Sundown Herbs brand), and about 0.5 part to about 1 part glycerin (preferably Humco brand).

For each 8 ounces of the cream base component, the composition preferably contains approximately 6000 to 12,000 IU of vitamin E (preferably Spring Valley brand), approximately 48,000 to 96,000 IU of vitamin A (preferably Spring Valley brand), and about 1000 to 2000 mg borage oil (preferably Sundown Herbs brand).

The vitamin E comprises dl-alpha tocopherol acetate and glycerin, which may contain vegetable oil. The vitamin A contains soybean oil, glycerin, water and fish liver oil. The ginseng contains soybean oil, glycerin, beeswax, ginseng extract, water, carob powder and silicon dioxide. The aloe vera gel contains aloe vera gel, triethanolamine, tocopherol acetate, carbomer 940, tetrasodium EDTA, DMDM hydantoin and diazolidinyl urea. The lanolin hydrous ingredients are lanolin and purified water. The gotu kola contains the herb gotu kola cellulose, calcium phosphate and magnesium stearate. Glycerin contains glycerin, USP 99.5% anhydrous. Borage oil comprises 200 mg gamma-linolenic acid.

The following examples are preferred embodiments of the skin rejuvenation cream or lotion compositions of the current invention. It is to be noted, however, that these examples are by no means limitations of the invention and that various modifications, and improvements in the manufacturing process, all fall under the scope of this invention.

EXAMPLE 1

Cream

| Personal Care Cream (Base) | 8 ounces (240 ml) |
|---|---|
| mink oil | 1 tbsp. (½ ounce or 15 ml) |
| vitamin E | 6,000 IU |
| vitamin A | 48,000 IU |
| borage oil | 1,000 mg |
| ginseng | 1,500 mg |
| aloe vera gel | 1 tpsp. (½ ounce or 15 ml) |
| lanolin hydrous | 1 tbsp. (½ ounce or 15 ml) |
| gotu kola | 900 mg |
| glycerin | 1 tbsp. (½ ounce or 15 ml) |

A preferred method of making the skin rejuvenation cream of example 1 comprises the following steps. The first step consists of combining mink oil and lanolin hydrous in a stainless steel receptacle, and heating the combination to 120° F. in order to melt it. Then mix the ingredients thoroughly for about 10 minutes. The second step consists of combining the mixture of the first step with aloe vera gel and glycerin while the original mixture is still warm. This combination should be mixed until blended. In the third step combine the vitamin E, vitamin A, gotu kola, borage oil, and ginseng with the combination of the second step, and add to the Personal Care Cream brand base. Heat this combination to 100° F. and mix thoroughly for 10 minutes or until a smooth and creamy consistency is reached. The fourth step consists of pouring the combination of the third step into an appropriate receptacle and cooling it. The resulting cream is excellent for use with normal skin.

EXAMPLE 2

Cream

| Personal Care Cream (Base) | 8 ounces (240 ml) |
|---|---|
| mink oil | 2 tbsp. (1 ounce or 30 ml) |
| vitamin E | 12,000 IU |
| vitamin A | 96,000 IU |
| borage oil | 2,000 mg |
| ginseng | 3,000 mg |
| aloe vera gel | 2 tbsp. (1 ounce or 30 ml) |
| lanolin hydrous | 2 tbsp. (1 ounce or 30 ml) |
| gotu kola | 1,800 mg |
| glycerin | 2 tbsp. (1 ounce or 30 ml) |

The preferred method of making the skin rejuvenation cream of example 2 is the same as in example 1. This cream works particularly well for very dry or mature skin.

EXAMPLE 3

Cream

| Personal Care Cream (Base) | 8 ounces (240 ml) |
|---|---|
| mink oil | 1 tbsp. (½ ounce or 15 ml) |
| vitamin E | 6,000 IU |
| vitamin A | 48,000 IU |
| ginseng | 1,500 mg |
| aloe vera gel | 1 tbsp. (½ ounce or 15 ml) |
| lanolin hydrous | 1 tbsp. (½ ounce or 15 ml) |
| gotu kola | 900 mg |
| glycerin | 1 tbsp. (½ ounce or 15 ml) |

The preferred method of making the skin rejuvenation cream of example 3 is the same as in example 1.

EXAMPLE 4

Cream

| Personal Care Cream (Base) | 8 ounces (240 ml) |
|---|---|
| mink oil | 2 tbsp. (1 ounce or 30 ml) |
| vitamin E | 12,000 IU |

-continued

| Personal Care Cream (Base) | 8 ounces (240 ml) |
|---|---|
| vitamin A | 96,000 IU |
| ginseng | 3,000 mg |
| aloe vera gel | 2 tbsp. (1 ounce or 30 ml) |
| lanolin hydrous | 2 tbsp. (1 ounce or 30 ml) |
| gotu kola | 1,800 mg |
| glycerin | 2 tbsp. (1 ounce or 30 ml). |

The preferred method of making the skin rejuvenation cream of example 4 is the same as in example 1.

EXAMPLE 5

Lotion

| skin rejuvenation cream of example 2 or | |
|---|---|
| example 4 | 4 ounces (120 ml) |
| glycerin | 2 tbsp. (1 ounce or 30 ml) |
| water | 6 tbsp. (3 oz. or 90 ml) |

A preferred method of making the skin rejuvenation cream of example 5 involves combining the skin rejuvenation cream composition of example 2 or example 4 with glycerine and water in a stainless steel receptacle. The combination is then heated to about 100° F., and mixed until creamy.

EXAMPLE 6

Cream

| skin rejuvenation cream of example 2 or | |
|---|---|
| example 4 | 4 ounces (120 ml) |
| citric acid | 1 ounce (30 ml) |
| corn starch | 2 tsp. (10 ml) |

A preferred method of making the skin rejuvenation cream of example 6 involves combining the skin rejuvenation cream composition of example 2 or example 4 with citric acid and corn starch, heating the combination to about 100° F., and mixing until creamy. The addition of corn starch helps to prevent separation.

EXAMPLE 7

Cream

| skin rejuvenation cream of example 2 or | |
|---|---|
| example 4 | 4 ounces (120 ml) |
| ascorbic acid | 1 ounce (30 ml) |
| corn starch | ½ tsp. (2.5 ml) |

A preferred method of making the skin rejuvenation cream of example 7 involves combining the skin rejuvenation cream composition of example 2 or example 4 with ascorbic acid and corn starch, heating the combination to about 100° F., and mixing until creamy.

EXAMPLE 8

Cream

| skin rejuvenation cream of example 2 or | |
|---|---|
| example 4 | 4 ounces (120 ml) |
| citric acid/ascorbic acid | 1 ounce (30 ml) |
| corn starch | 1 tsp. (5 ml) |

A preferred method of making the skin rejuvenation cream of example 8 involves combining the skin rejuvenation cream composition of example 2 or example 4 with citric acid, ascorbic acid, and corn starch; heating the combination to about 100° F.; and mixing until creamy.

In examples 6–8, the percent of acid may range anywhere from 12% to 20%.

EXAMPLE 9

Cream

| skin rejuvenation cream of example 2 or. | |
|---|---|
| example 4 | 4 ounces (120 ml) |
| animal/vegetable shortening | 1 ounce (30 ml) |

A preferred method of making the skin rejuvenation cream of example 9 involves combining the skin rejuvenation cream composition of example 2 or example 4 with animal/vegetable shortening, heating the combination to about 100° F., and mixing until creamy.

The composition of the present invention has a pleasant feel to the skin. Applied daily, it works well to smooth fine lines and wrinkles, reducing the signs of aging. The composition leaves the skin feeling soft and silky to the touch. The composition moisturizes without causing acne breakouts.

It is to be understood that the present invention is not limited to the sole embodiments described above, but encompasses any and all embodiments within the scope of the following claims.

I claim:
1. A topical skin rejuvenation composition comprising:
a cream base component, wherein for each 8 ounces of the cream base component, the composition comprises:
about ½ ounce to about 1 ounce of the mink oil;
about 6000 IU to about 12,000 IU of the vitamin E;
about 48,000 IU to about 96,000 IU of the vitamin A;
about 1500 mg to about 3000 mg of the ginseng;
about ½ ounce to about 1 ounce of the aloe vera gel;
about ½ ounce to about 1 ounce of the lanolin hydrous;
about 900 mg to about 1800 mg of the gotu kola; and
about 0.5 ounce to about 1 ounce of the glycerin.
2. The composition of claim 1, wherein the cream base component comprises deionized water, stearic acid, cetyl alcohol, isopropyl alcohol, isopropyl myristate, propylene glycol, retinol acetate, stearyl alcohol, glycerol stearate, dimethicone, hydrolyzed animal protein, lactic acid, carbomer 934, triethanolamine, methylparaben, quaternium-15, propylparaben, and fragrance.

3. The composition of claim 1, wherein for each 8 ounces of the cream base component, the composition comprises:
   about ½ ounce of the mink oil;
   about 6000 IU of the vitamin E;
   about 48,000 IU of the vitamin A;
   about 1500 mg of the ginseng;
   about ½ ounce of the aloe vera gel;
   about ½ ounce of the lanolin hydrous;
   about 900 mg of the gotu kola; and
   about 0.5 ounce of the glycerin.

4. The composition of claim 1, wherein for each 8 ounces of the cream base component, the composition comprises:
   about 1 ounce of the mink oil;
   about 12,000 IU of the vitamin E;
   about 96,000 IU of the vitamin A;
   about 3000 mg of the ginseng;
   about 1 ounce of the aloe vera gel;
   about 1 ounce of the lanolin hydrous;
   about 1800 mg of the gotu kola; and
   about 1 ounce of the glycerin.

5. The composition of claim 1, wherein for each 8 ounces of the cream base component, the composition further comprises about 1000 mg to about 2000 mg of borage oil.

6. The composition of claim 5, wherein for each 8 ounces of the cream base component, the composition comprises about 1000 mg of borage oil.

7. The composition of claim 5, wherein for each 8 ounces of the cream base component, the composition includes about 2000 mg of borage oil.

* * * * *